United States Patent [19]
Atherton et al.

[11] 4,143,134
[45] * Mar. 6, 1979

[54] HALO-PHOSPHONOPEPTIDES

[75] Inventors: Frank R. Atherton, Welwyn Garden City; Michael J. Hall; Cedric H. Hassall, both of Welwyn; Robert W. Lambert, Welwyn; Peter S. Ringrose, Harston, all of England

[73] Assignee: Hoffmann-La Roche Inc., Nutley, N.J.

[*] Notice: The portion of the term of this patent subsequent to Apr. 5, 1994, has been disclaimed.

[21] Appl. No.: 815,130

[22] Filed: Jul. 13, 1977

[30] Foreign Application Priority Data

Jul. 21, 1976 [GB] United Kingdom ............... 30347/76

[51] Int. Cl.² .................... A61K 37/00; C07C 103/52
[52] U.S. Cl. .............................. 424/177; 260/112.5 R
[58] Field of Search .................. 260/112.5 R; 424/177

[56] References Cited

U.S. PATENT DOCUMENTS 4,016,148   4/1977   Atherton et al. ............. 260/112.5 R Primary Examiner—Delbert R. Phillips
Assistant Examiner—Blondel Hazel
Attorney, Agent, or Firm—Jon S. Saxe; Bernard S. Leon; George M. Gould

[57] ABSTRACT

The present disclosure relates to halo-phosphonopeptides. The subject compounds are antibacterial agents and also potentiate the activity of antibiotics.

13 Claims, No Drawings

HALO-PHOSPHONOPEPTIDES

BACKGROUND OF THE INVENTION

Peptide derivatives of phosphonic and phosphinic acids containing all amino acids other than glycine in the L-configuration are disclosed in U.S. Pat. No. 4,016,148 issued Apr. 5, 1977. These compounds are disclosed to be useful as potentiators of antibiotics including D-cycloserine.

British Pat. No. 1,356,723 describes an antibiotic SF-1293 which is a peptide phosphinic acid. However, this substance is distinguishable from the present compounds in that the phosphinic acid moiety is at the amino terminus in the prior art structure while it is at the carboxy terminus in the instant compounds. Additionally, while no indication is given in this patent as to the configuration of the amino acids, since the substance is produced by fermentation it is no doubt comprised exclusively of the natural or L-amino acids. Finally, the prior art compound is indicated to be an antibiotic primarily an anti-fungal agent with no indication of any potentiating effectiveness for other antibiotics.

A paper by Haricharan et al., J. Org. Chem. 40, 470 (1975) discloses the synthesis of dipeptides of aminophosphonic acids. The amino terminal amino acid in each instance is glycine which are compounds specifically excluded from the scope of the present invention due to the fact that $R^3$ in the instant compounds is other than hydrogen ($R^3$=hydrogen would provide glycine) and further by the requirement that the amino terminal amino acid have the D configuration.

The presence of 2-aminoethylphosphonic acid from hydrolyzates of fractions derived from marine invertebrates was reported by Quin, Biochemistry 4 (2), 324 (1965). It was indicated that this compound was present in protein materials but the amino group apparently was blocked and the structure of the peptide was indeterminate.

Phosphonopeptides have also been disclosed in prior copending applications as follows: Ser. No. 707,158, filed July 21, 1976; Ser. No. 793,326, filed May 3, 1977 and Ser. No. 793,327, filed May 3, 1977.

DESCRIPTION OF THE INVENTION

The peptide derivatives provided by the present invention are compounds of the general formula

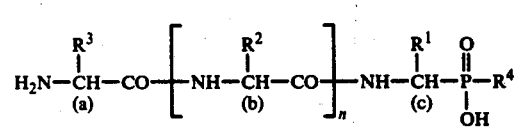

wherein $R^1$, $R^2$ and $R^3$ each represent the characterising group of an α-amino acid of the type normally found in proteins or a group of the formula —$CH_2X$ in which X represents a halogen atom with the proviso that at least one of $R^1$, $R^2$ and $R^3$ represents a group of the formula —$CH_2X$; $R^4$ represents a hydroxy or methyl group; n stands for zero, 1, 2 or 3; the configuration at the carbon atom designated as (a) is L or D,L (when $R^3 \neq H$); the configuration at the carbon atom designated as (b) is L or D,L (when $R^2 \neq H$); and the configuration at the carbon atom designated as (c) is (R) (when $R^1 \neq H$), and pharmaceutically acceptable salts thereof.

As used in this specification the term "the characterising group of an α-amino acid of the type normally found in proteins" means the residue R in a natural α-amino acid of the general formula

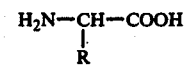

which is of the type normally occurring in proteins. Thus, for example, if the amino acid is glycine then the residue R represents a hydrogen atom and if the amino-acid is alanine then the residue R represents the methyl group. In leucine the residue R represents the isobutyl group, in phenylalanine the residue R represents the benzyl group and in glutamic acid the residue R represents the 2-carboxyethyl group. R can also represent a residue which is linked with the amino nitrogen (with the loss of one of the hydrogen atoms attached thereto), thus forming a nitrogen-containing ring such as in proline. The term "halogen" means fluorine, chlorine, bromine or iodine.

It will be appreciated that when n in formula I stands for 2 or 3, the value of $R^2$ can be the same or different.

When $R^1$ in formula I represents other than a hydrogen atom the configuration at the carbon atom designated as (c) is (R); that is to say, the configuration which would be obtained by replacing the carboxyl group of a naturally occurring L α-amino acid by a phosphorus moiety.

Preferred compounds of formula I hereinbefore are those in which $R^4$ represents a hydroxy group. Also preferred are compounds of formula I in which at least one of $R^1$, $R^2$ and $R^3$ represents a fluoromethyl [—$CH_2F$] or chloromethyl [—$CH_2Cl$] group. Yet again, compounds of formula I in which n stands for zero or 1 are preferred.

Examples of compounds of formula I are:
(D,L-3-fluoroalanylamino)-methylphosphonic acid, and
(1R)-1-(L-3-fluoroalanylamino)-ethylphosphonic acid.

According to the process provided by the present invention, the peptide derivatives aforesaid (i.e. the compounds of formula I and their pharmaceutically acceptable salts) are manufactured by (a) cleaving off by methods known per se the protecting group(s) present in a compound of the general formula

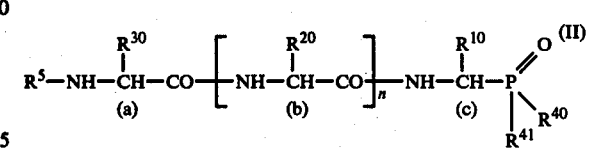

wherein $R^{10}$, $R^{20}$ and $R^{30}$ have any of the values accorded to $R^1$, $R^2$ and $R^3$ hereinbefore respectively except that any amino group (s) present may be in protected form and any other functional group which may be present in is protected form where required; $R^{40}$ represents a methyl group or $R^{41}$; $R^{41}$ represents a hydroxy group or lower alkoxy protecting group; $R^5$ represents a hydrogen atom or a protecting group; and n as well as the configurations at the carbon atoms designated as (a), (b) and (c) are as defined above, or (b) separating an (R,S)-diastereomeric compound corresponding to formula I into its diastereomers and isolating the (R)-diastereomer,
and, if desired, converting a compound of formula I obtained into a pharmaceutically acceptable salt.

The amino group or amino groups which may be present in $R^{10}$, $R^{20}$ or $R^{30}$ in formula II can be protected with any amino-protecting group which is well-known in peptide chemistry. Especially suitable amino-protecting groups for the purpose of the present invention are aralkoxycarbonyl groups, particularly the benzyloxycarbonyl group, and the tert.-butoxycarbonyl group. The amino-protecting group may also be a formyl, trityl or trifluoroacetyl group. Any carboxy or hydroxy group which may be present in $R^{10}$, $R^{20}$ or $R^{30}$ in formula II can be protected by a conventional carboxy-protecting or hydroxy-protecting group respectively. For example, a carboxy group may be protected by conversion into an alkyl ester (e.g. a tertbutyl ester) or an aralkyl ester (e.g. a benzyl ester). Again, for example, a hydroxy group may be protected, for example, by means of an aralkoxycarbonyl group (e.g. benzyloxycarbonyl), an alkanoyl group (e.g. acetyl, propionyl etc.), an aroyl group e.g. benzoyl), an alkyl group (e.g. tert.-butyl) or an aralkyl group (e.g. benzyl). The protection of other functional groups present in $R^{10}$, $R^{20}$ or $R^{30}$ may be carried out in a known manner. The protecting group denoted by $R^5$ in formula II can be any of the amino-protecting groups mentioned earlier in connection with $R^{10}$, $R^{20}$ and $R^{30}$.

The cleavage of the protecting group or protecting groups present in a compound of formula II is carried out in accordance with methods known per se; that is to say, methods in actual use for or described in the literature on the cleavage of protecting groups. Thus, for example, an aralkoxycarbonyl group (e.g. benzyloxycarbonyl) or a tert.-butoxycarbonyl group may be cleaved off by hydrolysis (e.g. treatment with a mixture of hydrogen bromide and glacial acetic acid). An aralkoxycarbonyl group (e.g. benzyloxycarbonyl) can also be cleaved off by hydrogenolysis (e.g. in the presence of palladium-on-charcoal or platinum oxide). The tert.-butoxycarbonyl group may also be cleaved off by means of hydrogen chloride in dioxan. A lower alkoxy group denoted by $R^{40}$ and/or $R^{41}$ can be a straight-chain or branched-chain alkoxy group which preferably contains from 1 to 6 carbon atoms and may be converted into a hydroxy group by treatment with a mixture of hydrogen bromide in glacial acetic acid or by means of trimethylchorosilane followed by aqueous hydrolysis. It will be appreciated that the cleavage of the protecting groups can be carried out in a single step or in more than one step depending on the nature of the protecting groups present.

The separation of an (R,S) diastereomeric compound corresponding to formula I into its diastereomers and isolation of the (R)-diastereomer can be carried out according to known methods; for example, by fractional crystallisation or by high pressure liquid chromatography.

Compounds of formula I are amphoteric in nature and form pharmaceutically acceptable salts with strong acids (e.g. methanesulphonic acid, p-toluenesulphonic acid, hydrochloric acid, hydrobromic acid, sulphuric acid etc.) and with bases (e.g. sodium hydroxide etc.).

The starting materials of formula II hereinbefore may be prepared, for example, by condensing a compound of the general formula

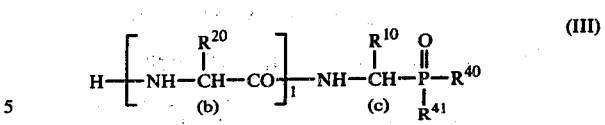

with a compound of the general formula

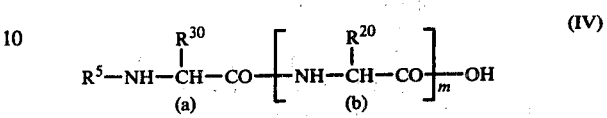

or with a reactive derivative thereof,
in which formulae l and m each stand for zero, 1, 2 or 3 with the proviso that the sum of l and m is zero, 1, 2 or 3; $R^5$, $R^{10}$, $R^{20}$, $R^{30}$, $R^{40}$ and $R^{41}$ have the significance given earlier; and the configuration at the carbon atoms designated as (a), (b) and (c) is as defined earlier.

Thus, when a compound of formula III in which l stands for zero is used, such a compound can be condensed with an appropriate compound of formula IV in which m stands for zero or a reactive derivative thereof to give a compound of formula II in which n stands for zero, or with an appropriate compound of formula IV in which m stands for 1 or a reactive derivative thereof to give a compound of formula II in which n stands for 1, or with an appropriate compound of formula IV in which m stands for 2 or a reactive derivative thereof to give a compound of formula II in which n stands for 2 or with an appropriate compound of formula IV in which m stands for 3 or a reactive derivative thereof to give a compound of formula II in which n stands for 3.

Again, a compound of formula III in which l stands for 1 can be condensed with an appropriate compound of formula IV in which m stands for zero or a reactive derivative thereof to give a compound of formula II in which n stands for 1, or with an appropriate compound of formula IV in which m stands for 1 or a reactive derivative thereof to give a compound of formula II in which n stands for 2 or with an appropriate compound of formula IV in which m stands for 2 or a reactive derivative thereof to give a compound of formula II in which n stands for 3.

Yet again, a compound of formula III in which l stands for 2 can be condensed with an appropriate compound of formula IV in which m stands for zero or a reactive derivative thereof to give a compound of formula II in which n stands for 2 or with an appropriate compound of formula IV in which m stands for 1 or a reactive derivative thereof to give a compound of formula II in which n stands for 3.

Finally, a compound of formula III in which l stands for 3 can be condensed with an appropriate compound of formula IV in which m stands for zero or a reactive derivative thereof to give a compound of formula II in which n stands for 3.

Alternatively, the compounds of formula II can be prepared by carrying out the foregoing condensation using an (R,S) compound corresponding to formula III and separating the (R) compound from the resulting (R,S) product in a manner known per se; for example, by crystallisation, chromatography or fractional crystallisation using a suitable base such as benzylamine.

The aforementioned condensation can be carried out in accordance with methods which are known per se in peptide chemistry; for example, by the mixed anhydride, azide, activated ester or acid chloride method.

In one method, an appropriate compound of formula III can be condensed with an appropriate compound of formula IV in which the terminal carboxy function is a mixed anhydride residue formed with an organic or inorganic acid. Suitably, a compound of formula IV carrying a free carboxy function is treated with a tertiary base such as a tri-(lower alkyl)-amine (e.g. triethylamine) or N-ethylmorpholine in an inert organic solvent (e.g. tetrahydrofuran, 1,2-dimethoxyethane, dichloromethane, toluene, petroleum ether or mixtures thereof) and the resulting salt is reacted with a chloroformic acid ester (e.g. the ethyl or isobutyl ester) at a low temperature. The mixed anhydride obtained is then suitably condensed in situ with the compound of formula III.

In another method, an appropriate compound of formula III can be condensed with an appropriate compound of formula IV in which the terminal carboxy group is in the form of an acid azide. This condensation is preferably carried out in an inert organic solvent such as dimethylformamide or ethyl acetate at a low temperature.

In yet another method, an appropriate compound of formula III can be condensed with an appropriate compound of formula IV in which the terminal carboxy function is in the form of an active ester group (e.g. the p-nitrophenyl, 2,4,5-trichlorophenyl or succinimido ester group). This condensation is suitably carried out in an inert solvent such as dimethylformamide aqueous dimethylformamide or an aqueous alkanol (e.g. aqueous ethanol).

In a further method, an appropriate compound of formula III can be condensed with an appropriate compound of formula IV in which the terminal carboxy function is in the form of an acid chloride. This condensation is preferably carried out in the presence of a base and at a low temperature.

The peptide derivatives provided by the present invention possess an antibacterial activity against gram-positive and gram-negative organisms such as, for example *Escherichia coli, Staphylococcus aureus, Serratia marcescens, Klebsiella aerogenes,* Enterobacter sp., *Streptococcus faecalis, Haemophilus influenzae* and *Salmonella typhimurium*. The following Table illustrates the minimum inhibitory concentration (M.I.C.) in μg/ml of a representative peptide derivative provided by this invention, namely (1R)-1-(L-3-fluoroalanylamino)-ethylphosphonic acid, in an in vitro test against various organisms.

Table

| Organism | M.I.C. (μg/ml) |
| --- | --- |
| *Escherichia coli* NCTC 10418 P.S. | 0.25 |
| *Escherichia coli* NCIB 8879 P.S. | 0.5 |
| *Klebsiella aerogenes* Type 33 Ba | 1.0 |
| *Klebsiella aerogenes* O-G KA1 | 4.0 |
| *Escherichia coli* C.1.5 P.R. | 4.0 |
| *Haemophilus influenzae* NCTC 4560 | 8.0 |

The peptide derivatives provided by this invention also potentiate the activity of antibiotics, including penicillin and cephalosporin antibiotics and D-cycloserine. Among the antibiotics which are potentiated by the present peptide derivatives there may be mentioned amoxycillin, cephradine, cephalothin, cephalexin, carbenicillin, ampicillin, penicillin G, sulbenicillin, cephazolin, cefoxitin, rifampicin, [(R)-1-(2-furoyloxy)-3-methylbutyl]-penicillin, (6R)-6-[[(hexahydro-1H-azepin-1-yl)-methylene]-amino]-pinicillanic acid, (pivaloyloxy) methyl (6R)-6-[[(hexahydro-1H-azepin-1-yl)-methylene]-amino]-penicillanate, cephamandole, cephaloridin, cephaloglycin, phenethicillin, methicillin, propicillin, ticarcillin, amoxycillan arginine salt, phosphonomycin, vancomycin and kanamycin.

The present invention thus also provides a pharmaceutical preparation containing a peptide derivative aforesaid, and, if desired, an antibiotic, in association with a compatible pharmaceutical carrier material.

The carrier material present in the pharmaceutical preparations provided by this invention can be any solid or liquid carrier material which is compatible with the peptide derivatives aforesaid, and with the antibiotics when such are present, and which is suitable for therapeutic administration. The carrier material can be an organic or inorganic carrier material which is suitable for enteral (e.g. oral) or parenteral administration. Examples of such carrier materials are water, gelatin, lactose, starches, magnesium stearate, talc, vegetable oils, gum arabic, polyalkyleneglycols, petroleum jelly etc. The pharmaceutical preparations can be made up in a solid form (e.g. as tablets, dragées, suppositories, or capsules) or in a liquid form (e.g. as solutions, suspensions or emulsions). The pharmaceutical preparations which can be prepared according to methods known in the art, may be subjected to conventional pharmaceutical operations such as sterilisation and may contain adjuvants such as preserving agents, stabilising agents, wetting agents, emulsifying agents, salts for varying the osmotic pressure or buffers. When a buffer is used, the pH of the pharmaceutical preparation will, of course, vary within a range which is well-known in pharmaceutical practice.

When the present pharmaceutical preparations contain a peptide derivative and an antibiotic, the weight ratio of peptide derivative to antibiotic can vary within wide limits. In general, the pharmaceutical preparations can contain the peptide derivative and antibiotic in a weight ratio of from 1:100 to 100:1, preferably in a weight ratio of from 1:64 to 64:1 and especially in a weight ratio of from 1:16 to 16:1.

The daily dosage of peptide derivative administered alone or in combination with an antibiotic will vary within wide limits depending on factors such as the particular peptide derivative chosen, the particular antibiotic chosen, the route of administration and the infection to be treated. For example, when a peptide derivative is administered alone, a daily dosage for oral administration may amount to about 2000 mg to 4000 mg and a daily dosage for parenteral administration may amount to about 800 mg to 2000 mg. When a peptide derivative is administered in combination with an antibiotic, a daily dosage for oral administration may amount to about 750 mg to 1500 mg of a combination of the peptide derivative and antibiotic and a daily dosage for parenteral administration may amount to about 200 mg to 2000 mg of a combination of peptide derivative and antibiotic. It will be appreciated that daily dosages can be administered in a single dosage or in divided dosages and that the dosages mentioned earlier may be varied upwards or downwards according to individual requirements and fitted to the exigencies of a particular situation as determined by the prescribing physician.

The following Examples illustrate the process provided by the present invention:

EXAMPLE 1

Ca. 40 mg of the monobenzylamine salt of (N-benzyloxycarbonyl-D,L-3-fluoroalanylamino)-methylphosphonic acid were dissolved in a minimum volume of 2 N ammonium hydroxide solution and passed down a column of 5 g of a sulfonated polystyrene cation exchange resin (Zerolit 225; freshly regenerated in the acid cycle). Elution was carried out using water. To the acid eluate (ca. 50 ml) were added 0.1 g of 5% palladium-on-charcoal catalyst, ca. 50 ml of methanol and one drop of glacial acetic acid. The mixture was hydrogenated overnight at room temperature and atmospheric pressure. After completion of the hydrogenation, the catalyst was filtered off and the filtrate evaporated to give a gum. This gum was dried over phosphorus pentoxide at 60° C. for 2 hours and was then triturated to give (D,L-3-fluoroalanylamino)-methylphosphonic acid as an off-white solid of melting point ca. 150° C. (decomposition). The structure of this product was confirmed by nuclear magnetic resonance spectroscopy.

The starting material was prepared as follows.

(i) A solution of 0.535 g (5 mmol) of D,L-3-fluoroalanine in 1.25 ml (5 mmol) of 4 N sodium hydroxide was stirred at 5° C. while 0.935 g (5.5 mmol) of benzyl chloroformate and 1.5 ml (6 mmol) of 4 N sodium hydroxide were added alternately in five portions of each and while maintaining the temperature at below 10° C. and the pH at greater than 11. The mixture was stirred for a further 1 hour at 0° C. as the temperature was allowed to rise to room temperature. The mixture was stirred overnight at room temperature. 2 ml of ether were then added and the resulting mixture was stirred vigorously at room temperature for 1 hour. The organic and aqueous layers were separated and the aqueous layer was extracted with 5 ml of ether. The aqueous layer was cooled to 10° C. and treated dropwise with 1.2 ml of 5 N hydrochloric acid until the mixture became acid to Congo Red. The mixture was then stirred for a further 2 hours at 10° C. when a solid crystallised from the solution. This solid was filtered off and washed with a minimum volume of ice-cold water. The solid was dissolved in 10 ml of ether and the solution washed with two 10 ml portions of cold (0° C.) water. The ether solution was dried over sodium sulphate and evaporated to yield a solid which was triturated with petroleum ether. The solid was filtered off and dried to give 0.6 g of product of melting point 108°–110° C. (decomposition). Recrystallisation of 0.1 g of this product from a mixture of 0.5 ml of ether and 0.5 ml of petroleum ether gave ca. 60 mg of N-benzyloxycarbonyl-D,L-3-fluoroalanine of melting point 112°–114° C. (decomposition).

(ii) 0.58 g (2.4 mmol) of N-benzyloxycarbonyl-D,L-3-fluoroalanine was stirred at 0° C. in 10 ml of dimethoxyethane while 0.276 g (2.4 mmol) of N-hydroxysuccinimide followed by 0.49 g (2.4 mmol) of dicyclohexylcarbodiimide were added. A precipitate was observed after stirring for a further 5 minutes. The mixture was stirred for a further 24 hours at 0° C. and then left to stand at 0° C. for 16 hours. The precipitate was filtered off and washed with dimethoxyethane. The combined filtrate and washing were evaporated and then re-evaporated with ether. Trituration with ether afforded 0.62 g of a solid of melting point 116°–120° C. (decomposition) which was recrystallised from 10 ml of isopropanol to yield 0.51 g of the succinimido ester of N-benzyloxycarbonyl-D,L-3-fluoroalanine of melting point 119°–120° C. (decomposition).

(iii) Ca. 0.5 g (1.5 mmol) of the succinimido ester of N-benzyloxycarbonyl-D,L-3-fluoroalanine was dissolved in 10 ml of warm ethanol and the solution was added at 5° C. to a stirred mixture, also at 5° C., of 0.67 g (6 mmol) of aminomethylphosphonic acid in a mixture of 12 ml of water and 6 ml of ethanol to which 1.12 g (13.5 mmol) of sodium bicarbonate had been added.

The mixture was stirred for 1 hour and the temperature was allowed to rise to room temperature. The mixture was subsequently stirred for ca. 60 hours at room temperature. The mixture was not homogeneous, and was therefore stirred at room temperature for a further 24 hours. The still heterogeneous mixture was evaporated, the residue dissolved in 50 ml of water and the solution extracted with 50 ml of chloroform and then twice with 25 ml of chloroform each time. The aqueous phase was separated, acidified to pH 2 with 2 N hydrochloric acid and then extracted with one 50 ml portion and subsequently with two 25 ml portions of ether, followed by one 50 ml portion and subsequently two 25 ml portions of chloroform. The aqueous layer was then evaporated, the residue taken up in a minimum volume of water and passed down a column of 50 g of a sulfonated polystyrene cation exchange resin (Zerolit 225; freshly regenerated in the acid cycle). Elution with three 50 ml portions of water afforded three acidic fractions, only the first of which contained the desired product. This fraction was evaporated and re-evaporated to remove hydrogen chloride. The residual gum was dissolved in water and titrated with 1 M aqueous benzylamine solution to pH 4.5. The solution was evaporated to give a solid which was recrystallised from 3 ml of water. The product was filtered off, washed with water until the filtrate was free from chloride ion, then washed with ethanol and subsequently with ether to give 0.030 g of the monobenzylamine salt of (N-benzyloxycarbonyl-D,L-3-fluoroalanylamino)-methylphosphonic acid. Evaporation of the mother liquors and washes and crystallisation of the residue from a mixture of 2 ml of water and 4 ml of ethanol removed 40 mg of aminomethylphosphonic acid. Evaporation of the filtrate and crystallisation of the residue from water afforded a further 10 mg of the desired monobenzylamine salt.

EXAMPLE 2

Ca. 0.3 g (0,66 mmol) of the monobenzylamine salt of (1R)-1-(N-benzyloxycarbonyl-L-3-fluoroalanylamino)-ethylphosphonic acid was dissolved in the minimum volume of 2 N ammonium hydroxide and passed down a column of 15 g of a sulfonated polystyrene cation exchange resin (Zerolit 225; freshly regenerated in the acid cycle). Elution was carried out with a methanol/water (1:1) mixture. To the acid eluate (ca. 100 ml) were added 0.3 g of 10% palladium-on-charcoal catalyst, 100 ml of methanol and three drops of glacial acetic acid. The mixture was hydrogenated for ca. 60 hours at room temperature and atmospheric pressure. After completion of the hydrogenation, the catalyst was filtered off. The filtrate was evaporated and then re-evaporated twice with n-propanol and once with ether. The residue was triturated with ether to give 80 mg of a pink solid of melting point ca. 150° C. (decomposition). Recrystallisation from a mixture of 1.5 ml of water and 4.5 ml of ethanol gave 30 mg of (1R)-1-(L-3-fluoroalanylamino)- ethylphosphonic acid of melting point 245° C. (decomposition); $[\alpha]_D^{20} = -30.4°$ (c = μ0.22% in water).

The starting material was prepared as follows.

(i) In a manner analogous to that described in Example 1, from 2.9 g (27 mmol) of L-3-fluoroalanine and 5.1 g (30 mmol) of benzyl chloroformate there were obtained 4.4 g of N-benzyloxycarbonyl-L-3-fluoroalanine of melting point 110°–116° C. (decomposition; softening at 140° C.), $[\alpha]_D^{20} = +5.4°$ (c = 0.5% in glacial acetic acid). Recrystallisation from a mixture of 25 ml of ether and 25 ml of petroleum ether gave 3.7 g of N-benzyloxycarbonyl-L-3-fluoroalanine of melting point 108°–115° C. (decomposition; softening at 104° C.); $[\alpha]_D^{20} = +5.6°$ (c = 0.5% in glacial acetic acid).

(ii) In a manner analogous to that described in Example 1, from 3.6 g (15 mmol) of N-benzyloxycarbonyl-L-3-fluoroalanine, 1.7 g (15 mmol) of N-hydroxysuccinimide and 3.4 g (16.4 mmol) of dicyclohexylcarbodiimide there were obtained 5.0 g of the succinimido ester of N-benzyloxycarbonyl-L-3-fluoroalanine of melting point 134°–138° C. (decomposition). Recrystallisation of a 0.5 g sample from 12 ml of isopropanol gave 0.4 g of the pure succinimido ester of melting point 138°–139° C. (decomposition); $[\alpha]_D^{20} = -37.5°$ (c = 0.5% in ethanol).

(iii) 1.7 g (13 mmol) of (1R)-1-aminoethylphosphonic acid were stirred in a mixture of 13 ml of water, 26 ml of dimethylformamide and 3.7 ml (27 mmol) of triethylamine at 0° C. while 4.5 g (13 mmol) of the succinimido ester of N-benzyloxycarbonyl-L-3-fluoroalanine were added as a solid in a single portion. The resulting heterogeneous mixture was stirred for 2 hours at 0° C. and then overnight at room temperature. The almost homogeneous mixture thus obtained was filtered to remove a small amount (0.19 g) of white solid. The filtrate was evaporated under an oil-pump vacuum to remove the solvents. The residual gum was dissolved in a minimum volume (ca 50 ml) of ethanol/water (1:1) and passed down a column of 50 g of a sulfonated polystyrene cation exchange resin (Zerolit 225; freshly regenerated in the acid cycle). Elution with ethanol/water (1:1) gave ca.200 ml of acid eluate which was evaporated. The resulting gum was partitioned between 100 ml of water and 100 ml of ether. The aqueous layer was extracted with 50 ml of ether. The ether phases were back-washed with water. The combined aqueous extracts were titrated to pH 4.5 with 4 M aqueous benzylamine and the solution was evaporated. The resulting gum-like solid was re-evaporated twice with ethanol and was then triturated with ethanol to give, after filtration, 1.15 g of a hygroscopic solid of melting point 196°–205° C. (decomposition). Recrystallisation of this solid from a mixture of 4 ml of water, 8 ml of ethanol and 8 ml of ether gave ca.0.3 g (Crop 1) of the monobenzylamine salt of (1R)-1-(N-benzyloxycarbonyl-L-3-fluoroalanylamino)-ethylphosphonic acid as a gelatinous solid of melting point 205°–215° C. (decomposition). Working-up of the mother liquors yielded a further 0.75 g (Crop 2) of the monobenzylamine salt of (1R)-1-(N-benzyloxycarbonyl-L-3-fluoroalanylamino)-ethylphosphonic acid.

The following Example illustrates a typical pharmaceutical preparation containing a peptide derivative provided by the present invention:

EXAMPLE 3

A 1000 ml injection solution containing the following ingredients was prepared:

| Ingredient | Per 1000 ml |
|---|---|
| Peptide derivative | 100.0 g |
| Chlorocresol | 1.0 g |
| Acetic acid (glacial) | 1.2 g |
| Sodium hydroxide solution (0.1 N) q.s. ad pH | 4.5 |
| Water for injection | ad 1000 ml |

The peptide derivative was dissolved in 500 ml of water and there was added to the solution formed a solution of the chlorocresol in 200 ml of water for injection. Then, the acetic acid was added while stirring. The resulting solution was adjusted to pH 4.5 with 0.1 N sodium hydroxide in water for injection while stirring. The solution obtained was made up to 1000 ml with water for injection, filtered through a sterile 0.22 micron membrane filter and filled into ampoules which were sealed and then sterilised in an autoclave at 121° C. for 20 minutes.

We claim:

1. Peptide derivatives of the formula

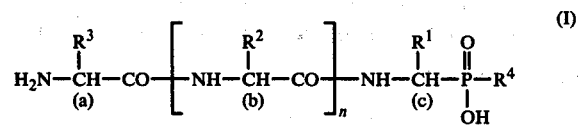

wherein $R^1$, $R^2$ and $R^3$ each is the characterising group of an α-amino acid of the type normally found in proteins selected from the group consisting of hydrogen, methyl, isobutyl, benzyl, 2-carboxyethyl and together with the adjacent CH and NH moieties form the ring structure of proline or —CH$_2$X in which X is halogen with the proviso that at least one of $R^1$, $R^2$ and $R^3$ is —CH$_2$X; $R^4$ is hydroxy or methyl; n is zero, 1, 2 or 3; the configuration at the carbon atom designated as (a) when $R^3$ is other than hydrogen is L or D,L; the configuration at the carbon atom designated as (b) when $R^2$ is other than hydrogen is L or D,L; and the configuration at the carbon atom designated as (c) when $R^1$ is other than hydrogen is (R), and pharmaceutically acceptable salts thereof.

2. Peptide derivatives of claim 1, wherein $R^4$ is hydroxy.

3. Peptide derivatives of claim 1 wherein at least one of $R^1$, $R^2$ and $R^3$ is fluoromethyl or chloromethyl.

4. Peptide derivatives of claim 3, wherein n is zero or 1.

5. The compound of claim 4 which is (D,L-3-fluoroalanylamino)-methylphosphonic acid.

6. The compound of claim 4 which is (1R)-1-(L-3-fluoroalanylamino)-ethylphosphonic acid.

7. A pharmaceutical preparation comprising an antibacterial effective amount of the peptide derivative or a salt thereof of claim 1 in association with a compatible pharmaceutical carrier material.

8. A pharmaceutical preparation comprising an antibiotic potentiating effective amount of a peptide derivative of claim 1, an effective amount of an antibiotic capable of being potentiated by said peptide derivative of claim 1 and a compatible pharmaceutical carrier material.

9. The pharmaceutical preparation of claim 8, wherein said antibiotic is selected from amoxycillin, cephradine, cephalothin, cephalexin, carbenicillin, ampicillin, penicillin G, sulbenicillin, cephazolin, cefoxitin, rifampicin, [(R)-1-(2-furoyloxy)-3-methylbutyl]-penicillin,(6R)-6-[[(hexahydro-1H-azepin-1-yl)-methylene]-amino]-penicillanic acid,(pivaloyloxy)-methyl(6R)-6-[[(hexahydro-1H-azepin-1-yl)-methylene]-amino]-penicillanate, cephamandole, cephaloridin, cephaloglycin, phenethicillin, methicillin, propicillin, ticarcillin, amoxycillin arginine salt, phosphonomycin, vancomycin or kanamycin.

10. The pharmaceutical preparation of claim 9 wherein the weight ratio of peptide derivative to antibiotic is from 1:100 to 100:1.

11. The pharmaceutical preparation of claim 9 wherein the weight ratio of peptide derivative to antibiotic is from 1:64 to 64:1.

12. The pharmaceutical preparation of claim 9 wherein the weight ratio of peptide derivative to antibiotic is from 1:16 to 16:1.

13. A compound of formula

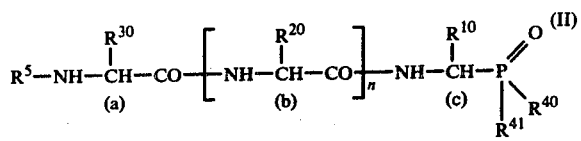

wherein $R^{10}$, $R^{20}$ and $R^{30}$ each is the characterising group of an α-amino acid of the type normally found in proteins selected from the group consisting of hydrogen, methyl, isobutyl, benzyl, 2-carboxyethyl and together with the adjacent CH and NH moieties form the ring structure of proline or —$CH_2X$ in which X is halogen with the proviso that at least one of $R^{10}$, $R^{20}$ and $R^{30}$ is —$CH_2X$, and wherein any amino or other functional group(s) present may be in protected form; $R^{40}$ is methyl or $R^{41}$; $R^{41}$ is a hydroxy or lower alkoxy protecting group; $R^5$ is hydrogen or a protecting group; n is zero, 1, 2 or 3; the configuration at the carbon atom designated as (a) when $R^3$ is other than hydrogen is L or D,L; the configuration at the carbon atom designated as (b) when $R^2$ is other than hydrogen is L or D,L; and the configuration at the carbon atom designated as (c) when $R^1$ is other than hydrogen is (R).

* * * * *